United States Patent
Traneus

(10) Patent No.: US 10,786,688 B2
(45) Date of Patent: Sep. 29, 2020

(54) SYSTEM AND METHOD FOR MODELLING OF SCATTERING IN ION RADIOTHERAPY TREATMENT PLANNING

(71) Applicant: RaySearch Laboratories AB, Stockholm (SE)

(72) Inventor: Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/471,919

(22) PCT Filed: Dec. 20, 2017

(86) PCT No.: PCT/EP2017/083802
§ 371 (c)(1),
(2) Date: Jun. 20, 2019

(87) PCT Pub. No.: WO2018/115114
PCT Pub. Date: Jun. 28, 2018

(65) Prior Publication Data
US 2020/0101321 A1    Apr. 2, 2020

(30) Foreign Application Priority Data
Dec. 22, 2016  (EP) .................................. 16206258

(51) Int. Cl.
*A61N 5/10*     (2006.01)
(52) U.S. Cl.
CPC .... *A61N 5/1031* (2013.01); *A61N 2005/1034* (2013.01); *A61N 2005/1087* (2013.01)
(58) Field of Classification Search
CPC .............................. A61N 5/103; A61N 5/1031

USPC .......................................................... 600/1–8
See application file for complete search history.

(56) References Cited

U.S. PATENT DOCUMENTS

2015/0352374 A1   12/2015 Gattiker et al.

OTHER PUBLICATIONS

Engdahl, Staffan, "Validation of Ion Therapy Dose Calculation Algorithms by Monte Carlo," Physics of Medical Imaging Department of Physics, KTH, Jan. 2015, retrieved from Internet: URL:http://www.diva-portal.org/smash/get/diva2:828498/FULLTEXT01.
Newhauser, Wayne D. et al., "The physics of proton therapy," Physics in Medicine & Biology, 60 (2015), R155-R209.
EP Search Report dated Jul. 7, 2017 for EP 16206258.2.

*Primary Examiner* — John P Lacyk
(74) *Attorney, Agent, or Firm* — Faegre Drinker Biddle & Reath LLP

(57) ABSTRACT

A method of evaluating a radiotherapy treatment plan for ion based radiotherapy, is proposed, comprising the steps of
determining multiple elastic scattering of ions for scattering angles in a first angular interval having an upper limit at a selected cut-off angle by means of a model for Coulomb scattering;
determining multiple elastic scattering of ions for scattering angles in a second angular interval having a lower limit at the selected cut-off angle;
determining the scattering for angles in a range comprising at least a part of the first angular interval and at least a part of the second angular interval, based on the results obtained for the first and second angular interval, respectively.
The method avoids the double counting of particles at large scattering angles that occurs when using conventional methods.

10 Claims, 2 Drawing Sheets

SYSTEM AND METHOD FOR MODELLING OF SCATTERING IN ION RADIOTHERAPY TREATMENT PLANNING

This application is the National Stage of International Application No. PCT/EP2017/083802, filed Dec. 20, 2017, and claims benefit of European Patent Application No. 16206258.2, filed Dec. 22, 2016, the entire contents of which are incorporated by reference herein.

TECHNICAL FIELD

The present invention relates to a system and a method for modelling the scattering of ions in radiotherapy treatment planning.

BACKGROUND

The delivery of a radiotherapy treatment plan to a patient is affected by a number of factors, an important one being the patient's own anatomy. Structural variations in the patient's body will lead to scattering of particles, altering their path and therefore affecting the resulting dose distribution. The density of the structures traversed by the ion will also affect the path length.

The invention is discussed here for use with protons but it should be clear that it can applied to other ions as well and is thus not restricted only to protons.

The elastic scattering of a proton on a nucleus is caused by the combined effect of two forces: the Coulomb force and the strong nuclear force. The Coulomb scattering between a proton and a nuclei is caused by electro-magnetic interaction between their electrical charges. The nuclear elastic scattering is caused by direct interaction between the proton and the nuclei through the strong force. In nature the two forces manifest as a single indistinguishable interaction and can in principle not be studied or measured isolated from each other.

The reason the scattering process is referred to as elastic scattering is that no kinetic energy is converted to internal excitation energy of the projectile or target.

Scattering from the Coulomb force dominates over the strong force at small forward angles. At large angles they are of similar amplitude.

A proton that passes through tissue undergoes of the order of millions elastic scattering interactions per centimetre of tissue. In radiotherapy calculations of, for example, dose the elastic scattering interactions are usually incorporated through so called multiple scattering theories. In such a theory the large number of elastic scatterings are condensed into a much smaller number of artificial "multiple scatterings" interactions.

Multiple scattering in the patient's tissue and the range shifter (if used) leads to a dilution of primary protons away from the brag peak region and generation of a halo of secondary ions due to scattering at larger angles relative to the direction of the incident proton. It is essential to model this phenomenon in sufficient detail to be able predict the dose deposition in a patient well. The amount of scattering depends on the tissue densities and compositions along the proton tracks. The scattering will lower the dose in the Bragg peak region, some times substantially. It will also result in an intricate dose variation with field size and field shape as the halo carries non-negligible amounts of energy away from the track of the incident proton. Thus, any computer program designed for the purpose of ion treatment planning must take multiple scattering into account.

Conventional methods exist for modelling electron and positron multiple scattering. For example, the Goudsmit-Saunderson (GS) theory for multiple scattering is traditionally applied to electron elastic scattering in some radiotherapy treatment planning systems. For proton therapy, such methods for modelling particle scattering typically yield incorrect results, especially in some angle ranges.

The GS theory models multiple scattering caused by the Coulomb force only. It does not include nuclear elastic scattering caused by the strong nuclear force.

SUMMARY OF THE INVENTION

It is an object of the present invention to achieve a reliable model for proton multiple scattering that reflects more correctly the scattering of protons and other ions in ion based radiotherapy.

The invention proposes a computer-based method for modelling multiple scattering in proton radiotherapy. The method comprises the steps of determining multiple elastic scattering of ions for scattering angles in a first angular interval having an upper limit at a selected cut-off angle by means of a model for Coulomb scattering;

determining multiple elastic scattering of ions for scattering angles in a second angular interval having a lower limit at the selected cut-off angle;

determining the scattering for angles in a range comprising at least a part of the first angular interval and at least a part of the second angular interval, based on the results obtained for the first and second angular interval, respectively.

The invention also relates to a method of dose calculation including modelling ion scattering by means of the inventive method.

The multiple elastic scattering in the first angular interval may be calculated by means of any model for Coulomb multiple scattering, for example, the Goudsmit-Saunderson model or the Moliere model.

The scattering angular distribution in the second angular interval may be determined based on angular differential cross sections from a database, or it may be calculated by a suitable model. Preferably, the scattering angular distribution in the second angular interval includes the effects of both Coulomb multiple scattering and scattering due to strong nuclear force.

The conventional method used in the art is to treat scattering due the two forces as two separate processes and superposing the effects. This gives reasonably correct results at forward angles where the Coulomb force dominates. However, at larger scattering angles, where the forces are of similar amplitude this leads to an inconsistent double count which will yield a misleading result.

This insight forms the starting point for the present invention which proposes a method to model multiple scattering while avoiding the double count. The method proposed to avoid the double counting is to modify the GS theory such that it is restricted to include Coulomb scattering angles up to a certain cut off angle instead of all angles between zero degrees up to 180 degrees. The cut off angle is chosen so that only the angle range where effects of the Coulomb force dominate is included. Then the nuclear elastic scattering contribution is added for angles above the cut off angle. The nuclear elastic scattering addition is specified by its angle differential cross section which can be based on experimental data or calculated by some model. In both cases, the input data for the nuclear elastic scattering contribution above the cut-off angle does reflect the net effect of both the Coulomb force and the nuclear force. Such data are published in the literature and are available for a number of elements over a wide range of incident proton energies.

The invention is most straightforwardly used in the context of a Monte Carlo based dose engine. In that case the method is used when sampling deflection angles during the simulating of the proton's path through the medium.

In summary, with the method according to the invention the double counting is avoided by applying a cut-off angle in the GS theory and adding a large angle elastic scattering contribution for angles above the cutoff. Thereby a single consistent formalism starting from the underlying fundamental elastic differential cross-sections is achieved with a result that correctly reflects the actual situation.

The cut-off angle is preferably selected such that the nuclear elastic scattering results in a higher scattering angle than the cut-off angle for a majority of particles scattered to angles where the Coulomb interaction does not dominate. Suitable cut-off angles have been found to be between 2 and 10 degrees, for example 5 degrees. In a preferred embodiment, the cut-off angle is selected in the interval between 1 and 15 degrees, preferably between 2 and 10 degrees.

The proposed method is straightforward to implement in Monte Carlo based dose calculation algorithms for use in treatment planning. It is also possible to include the method in analytical based dose calculation algorithms.

The invention also relates to a computer program product comprising computer readable code means which, when executed in a computer, will cause the computer to perform the method according to any embodiment of the method described above.

The invention also relates to a non-transitory computer readable medium encoded with computer executable instructions which, when run in a first computer device will cause the device to perform the method according to any embodiment of the method described above.

The invention also relates to a computer system comprising a processor, a data memory and a program memory, wherein the program memory comprises a computer program product or a non-transitory computer readable medium according to the above.

BRIEF DESCRIPTION OF THE DRAWINGS

The invention will be described in more detail in the following, by way of example and with reference to the appended drawings, in which.

BRIEF DESCRIPTION OF THE DRAWINGS

Figure 1:
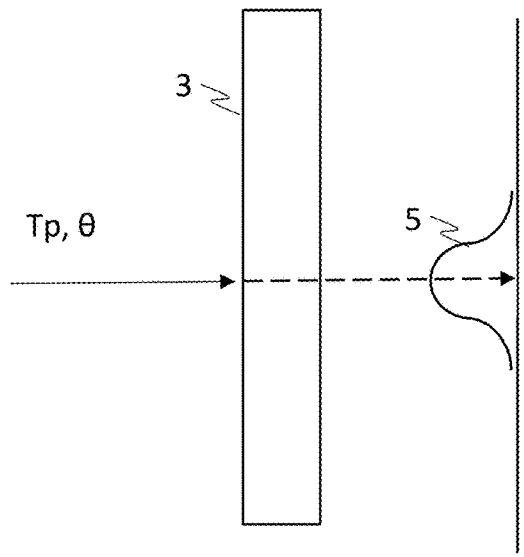
FIG. 1 illustrates multiple scattering of protons.

FIG. 1 illustrates multiple scattering of protons travelling through a body of water illustrated by a rectangular shape 3.

The particles, indicated by a horizontal arrow representing the incidental angle, all enter the water with the same energy Tp and at the same angle θ. The water will cause the particles to scatter so that instead of passing straight through the body 3 along the dashed line, the particles will follow paths that will be distributed around the incidental angle. As indicated by the distribution 5 the angles of the particles will form an approximatively Gaussian distribution. The actual scattering will be dependent on the material through which the particles travel as well as their energy Tp.

The scattering of the particles will be caused by different effects. When an incoming positive ion, such as a proton, passes near an oxygen nucleus in the water the forces acting between the proton and the nuclei causes the incoming ion to be deflected. This deflection will be mostly by a relatively small angle. The particles scattered by this effect will deposit energy in the target volume within a small area. A small fraction of the incoming positive ions will pass so near the oxygen nucleus that they will be deflected by a greater angle. The ions that are scattered by a greater angle will travel about the same distance as the ions that are scattered by a smaller angle, but will end somewhere outside of the Bragg peak, because of the larger scattering angle.

The invention involves applying an angle-restricted Goudsmit-Saunderson (GS) theory for multiple scattering to proton Monte Carlo dose calculations. In the GS theory, it is convenient to use a pre-calculated data set to be used when applying GS in a computer code. This data set is referred to as the q2-surface and describes scattering due to the Coulomb interaction by the relativistic Mott cross section. The q2-surface is produced in a preparative step where only scattering angles smaller than a predetermined cut-off angle is included. It would also be possible to perform the calculation of the data set during the modelling.

Figure 2:
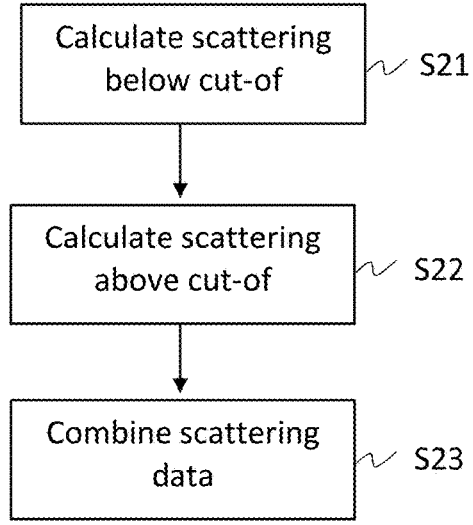
FIG. 2 is a flow chart of a method according to the invention.

FIG. 2 is a flow chart illustrating the overall method of the invention.

In step S21, multiple Coulomb scattering is calculated for elastic scattering below the cut-off angle. In step S22, elastic scattering is calculated for angles larger than the cut-off angle. In step S23, the data combined from the results of steps S21 and S22 are used.

Figure 3:
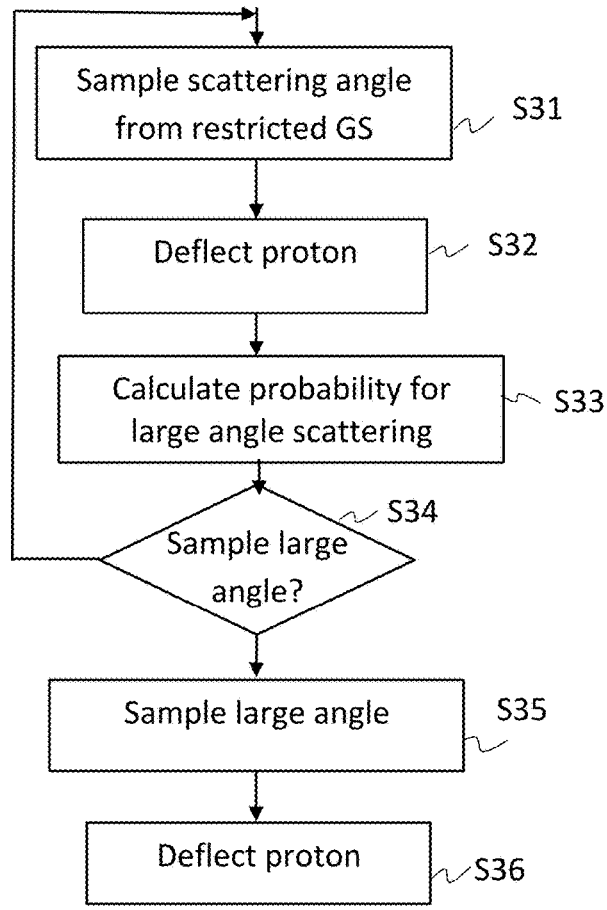
FIG. 3 is a flow chart of an embodiment of the invention as it may be implemented in a Monte Carlo dose calculating engine.

FIG. 3 is a flow chart of a method illustrating how the invention can be applied in a Monte Carlo based dose calculation code where protons are propagated until they have lost all their energy and stop. The method is applied when propagating a proton a certain small distance in tissue. The distance can be for instance across a dose voxel of size 3 mm.

In step S31, a multiple scattering angle is sampled from the angle-restricted GS theory and the direction of the proton is deflected accordingly.

In step S32, the direction of the proton is deflected according to the scattering angle sampled in step S31. Steps S31 and S32 correspond to step S21 in FIG. 2.

In step S33, the probability for a large angle elastic scattering event is calculated using the angular integrated double differential cross section integrated from the cut-off angle to 180 degrees. The nature of the problem is such that this probability will be small and of the order of a few percent (if the probability is significantly larger the procedure described here need to be modified)

In S34 it is determined by random sampling if a large angle scattering event shall occur based on the probability calculated in step S33.

In S35, if a large angle elastic scattering event shall occur a deflection angle is sampled from the double differential cross section, and in step S36, the direction of the proton is deflected accordingly. For instance, for water, the scattering events for large angles can be sampled from the proton-oxygen elastic differential cross-sections tabulated in the ENDF database. Steps S33-S36 correspond to step S22 in FIG. 2.

After step S36, the proton is either absorbed in the medium because it has lost all its energy or the procedure returns to step S31 for continued transport through the tissue.

The cut-off angle should be selected according to the field of application. For application in a proton Monte Carlo system a cut-off angle of approximately 5 degrees may be suitable, as this is the smallest angle for which proton-nuclear elastic cross-sections are tabulated in the ENDF database. In other applications a cut-off angle of approximately in the range 0.1 to 15 degrees, more specifically 2 to 7 degrees, may be suitable.

Figure 4:
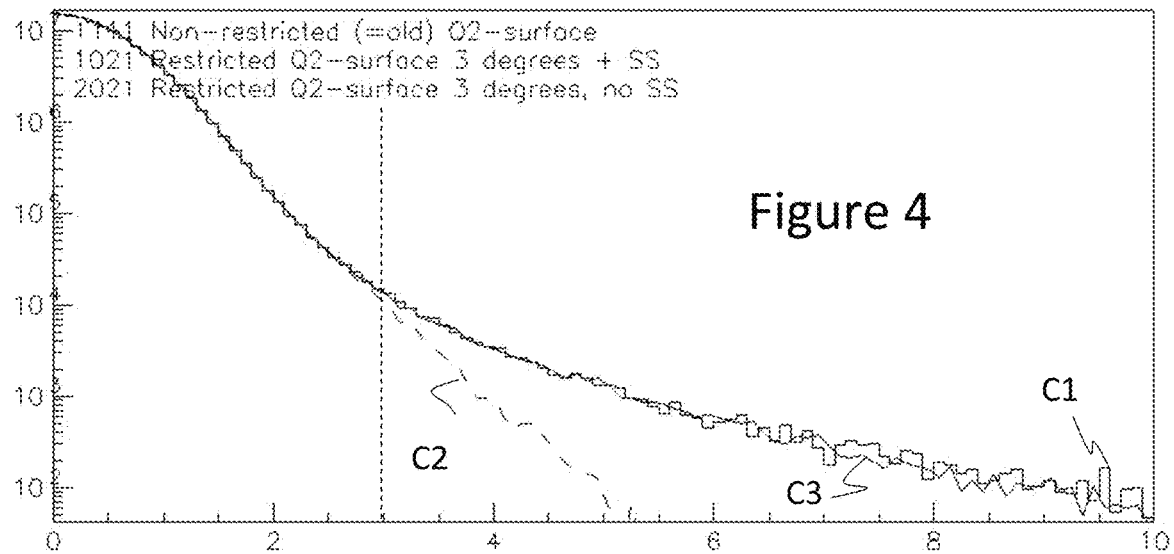
FIG. 4 illustrates an example of the GS sampling of protons

FIG. 4 illustrates the method when applied to 100 MeV protons in a 1 cm thick water slab. In FIG. 4 only the Coulomb force is considered and not nuclear elastic scattering. The horizontal axis shows deflection angle in degrees. The vertical axis shows the probability of a certain angle, on a logarithmic scale. The curve marked C1 shows the actual full GS multiple scattering angle distribution without restriction for all angles. In a real situation, this would not be known; the curve is included here merely to show the accuracy of the method. The curve C2, which falls more rapidly from about 3 degrees, shows the restricted GS angle distribution with a cut-off angle of 3 degrees, indicated by a dashed vertical line. The curve C3 shows the restricted GS curve with large angle single scattering added back according to the missing macroscopic Mott cross section. As can be seen, the C1 and C3 curves overlap for all angles.

Figure 5:
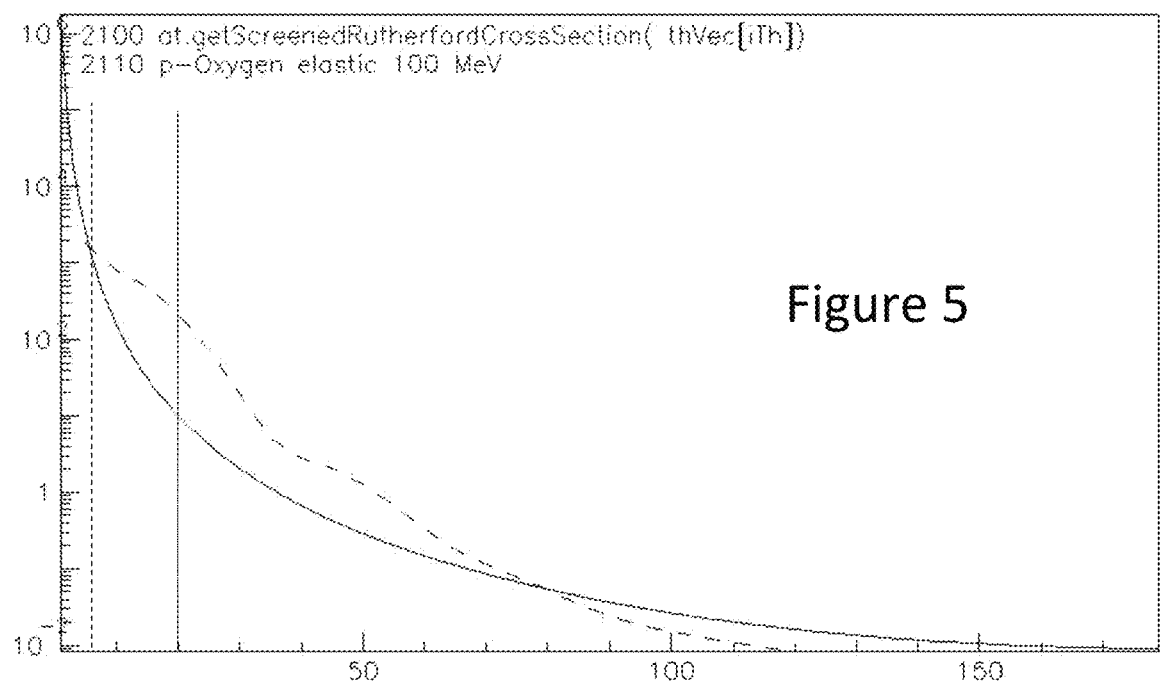
FIG. 5 shows representations of cross-sections that may be used for scattering calculations according to the invention.

FIG. 5 shows two different angle differential cross-sections: the so-called Mott cross section (solid line), which is the cross section for the Coulomb scattering, and a dashed curve with data for larger angles. The vertical dotted lines indicate scattering angles of 5 degrees and 20 degrees, respectively. As discussed above, over the whole angular range the actual cross section is the result of the combined effect of the Coulomb force and the strong force. For small angles the Coulomb force dominates. At the larger angles the two forces are of similar strength and combine in a complicated way resulting in the dashed line with wiggles characteristic for the target nuclei species as well as the energy of the incident proton. Note that the large angle part of the curve is sometimes referred to as the nuclear elastic part which is obviously not entirely correct as the Coulomb force also influences the variation with angle. The dashed curve representing the nuclear elastic cross section starts at a scattering angle of 5 degrees. For angles smaller than 5 degrees, the Coulomb interaction dominates. At the larger scattering angles the pure Mott cross section is clearly in disagreement with the actual cross section.

In the case shown in FIG. 5, the double counting of scattered particles is avoided in the range where it would cause the greatest error, in the area from 5 to 50 degrees. If the scattering were calculated using conventional methods, the error caused by double counting would be between 10% and 100% in this range.

The combined cross-section (not shown) will consist of the Mott cross section for angles below 5 degrees and the nuclear elastic cross section for angles above 5 degrees, which is the chosen cut-off angle in this example.

Figure 6:
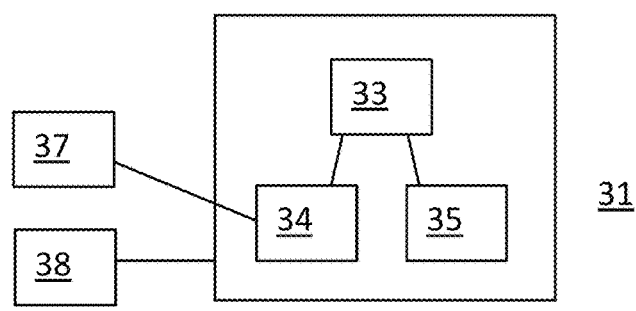
FIG. 6 illustrates a computer system in which the inventive method may be performed

FIG. 6 is a schematic representation of a computer system in which the inventive method may be performed. A computer 31 comprises a processor 33, a data memory 34 and a program memory 35. Preferably, user input means 37, 38 is also present, in the form of a keyboard, a mouse, a joystick, voice recognition means or any other available user input means.

A treatment plan to be evaluated is found in the data memory 34. The treatment plan may be generated in the computer 31, or received from another storage means in any way known in the art.

The data memory 34 typically holds various data related to the treatment plan. As will be understood, the data memory 34 is only shown schematically. There may be several data memory units, each holding one or more different types of data, for example, one data memory for the treatment plan, one for the CT scans, etc. The program memory 35 holds a computer program arranged to control the processor to perform the plan evaluation according to the invention.

The invention claimed is:

1. A method of modelling ion multiple scattering for planning of ion based radiotherapy, comprising the following steps, performed in a computer:
   determining multiple elastic scattering of ions for scattering angles in a first angular interval having an upper limit at a selected cut-off angle by means of a model for Coulomb scattering;
   determining multiple elastic scattering of ions for scattering angles in a second angular interval having a lower limit at the selected cut-off angle to reflect the net effect of both a Coulomb force and a nuclear force in the second angular interval;
   determining, as a model for ion multiple scattering, the scattering for angles in a range comprising at least a part of the first angular interval and at least a part of the second angular interval, based on the results obtained for the first and second angular intervals, respectively; and
   using the model for ion multiple scattering to calculate dose for use in creating ion based radiotherapy treatment plans.

2. The method according to claim 1, wherein the cut-off angle is selected such that the nuclear elastic scattering results in a higher scattering angle than the cut-off angle for a majority of particles scattered to angles where the Coulomb interaction does not dominate.

3. The method according to claim 1, wherein the multiple elastic scattering in the first angular interval is performed by means of a model for Coulomb multiple scattering.

4. The method according to claim 1, wherein the multiple elastic scattering in the first angular interval is determined according to the Goudsmit-Saunderson model.

5. The method according to claim 1, wherein the scattering angular distribution in the second angular interval is determined based on angular differential cross sections from a database or calculated by a suitable model.

6. The method according to claim 1, wherein the cut-off angle is selected in the interval between 1 and 15 degrees.

7. A computer program product comprising computer readable code means which, when executed in a computer, will cause the computer to perform the method according to claim 1.

8. A non-transitory computer readable medium encoded with computer executable instructions which, when run in a first computer device will cause the device to perform the method according to claim 1.

9. A computer system comprising a processor, a data memory and a program memory, wherein the program memory comprises a non-transitory computer readable medium according to claim 8.

10. The method according to claim 6, wherein the selected cut-off angle is 5 degrees.

* * * * *